US00PP22536P2

(12) United States Plant Patent
Brown

(10) Patent No.: US PP22,536 P2
(45) Date of Patent: Feb. 28, 2012

(54) ***ANTIRRHINUM* PLANT NAMED 'AACOR01'**

(50) Latin Name: *Antirrhinum majus*
Varietal Denomination: AACOR01

(76) Inventor: Graham Noel Brown, Pennant Hills (AU)

( * ) Notice: Subject to any disclaimer, the term of this patent is extended or adjusted under 35 U.S.C. 154(b) by 0 days.

(21) Appl. No.: 12/802,076

(22) Filed: May 28, 2010

(51) Int. Cl.
*A01H 5/00* (2006.01)

(52) U.S. Cl. ..... Plt./322

(58) Field of Classification Search ..... Plt./322
See application file for complete search history.

*Primary Examiner* — Kent L Bell
(74) *Attorney, Agent, or Firm* — Cassandra Bright

(57) ABSTRACT

A new and distinct *Antirrhinum* cultivar named 'AACOR01' is disclosed, characterized a compact, mounding plant habit and flexible stems. The new variety is an *Antirrhinum*, typically produced as a garden or container plant.

1 Drawing Sheet

Figure 1:
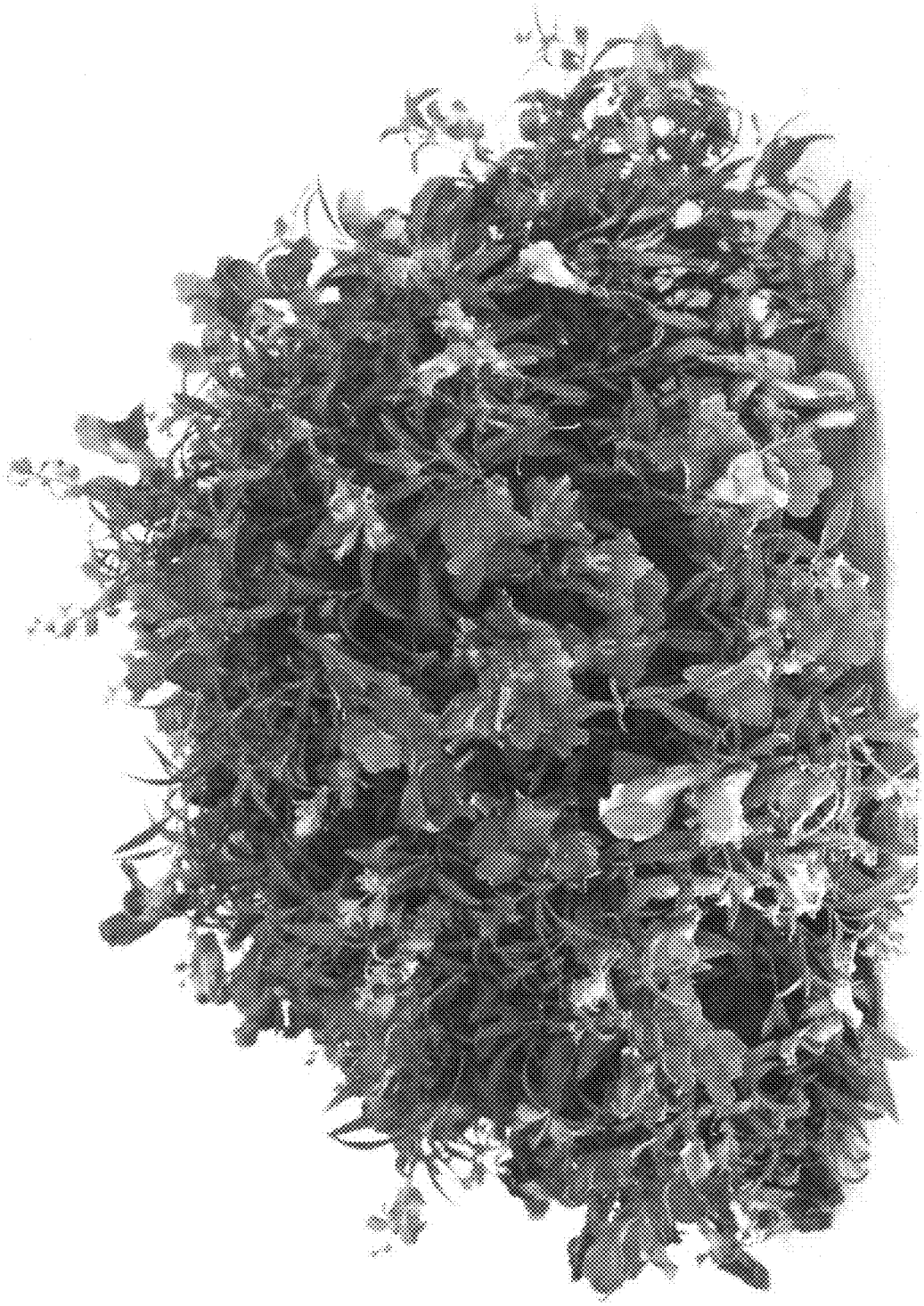

Latin name of the genus and species: *Antirrhinum majus.*
Variety denomination: 'AACOR01'.

BACKGROUND OF THE INVENTION

The new cultivar is a product of a planned breeding program. The new variety originated from a cross pollination of the seed parent, an unnamed, unpatented proprietary selection of *Antirrhinum majus* with the pollen parent a different unnamed, unpatented *Antirrhinum majus*. The crossing was made during November of 2005, at a commercial greenhouse in New South Wales Australia. 'AACOR01' was discovered by the inventor, Graham Brown, a citizen of Australia, in New South Wales, at a commercial greenhouse during November of 2007.

Asexual reproduction of the new cultivar 'AACOR01' was first performed in New South Wales, Australia, at a commercial greenhouse by vegetative cuttings in November 2007. 'AACOR01' has since produced several generations and has shown that the unique features of this cultivar are stable and reproduced true to type.

SUMMARY OF THE INVENTION

The cultivar 'AACOR01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AACOR01.' These characteristics in combination distinguish 'AACOR01' as a new and distinct *Antirrhinum* cultivar:

1. Compact, mounded plant habit.
2. Early flowering.
3. Flexible, non-brittle stems.

PARENTAL COMPARISON

Plants of the new cultivar 'AACOR01' are similar to the female parent in most horticultural characteristics. However, 'AACOR01' differs in producing a compact, mounding plant, whereas the seed parent has a trailing plant habit. Additionally, the seed parent flowers three weeks later than the new variety.

Plants of the new cultivar 'AACOR01' are similar to the male parent in most horticultural characteristics. However, 'AACOR01' differs in having a compact, mounded plant habit, whereas the pollen has a distinctively upright plant habit.

COMMERCIAL COMPARISON

'AACOR01' can be compared to the commercial variety *Antirrhinum majus* 'Balumdepur' U.S. Plant Pat. No. 13,097. Plants of 'Balumdepur' are similar to plants of 'AACOR01' in most horticultural characteristics, however, 'AACOR01' produces a flower with a lighter color, and stems that are less brittle.

BRIEF DESCRIPTION OF THE PHOTOGRAPH

The accompanying photograph in FIG. 1 illustrates in full color a typical plant of 'AACOR01' grown outdoors in Lompoc, Calif. This plant is approximately 6 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2001, except where general terms of ordinary dictionary significance are used. The following observations and measurements describe 'AACOR01' plants in a commercial greenhouse in Bodger, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Antirrhinum majus* 'AACOR01'.
Age of the plant described: Approximately 6 months.
Container size of the plant described: 6 inch.

PROPAGATION

Time to initiate roots: About 10 days at approximately 25° C.
Root description: Fibrous
Propagation method: Vegetative cuttings.

PLANT

Growth habit: Mounding annual.
Container size: 6" pot.
Height: Measured from top of soil line of pot, approximately 15 cm.
Plant spread: Approximately 45 cm.
Growth rate: Rapid.
Branching characteristics: Very free branching.
Lateral branches:
*Length.*—Approximately 19 cm.
*Diameter.*—Approximately 0.4 cm.
*Texture.*—Glabrous.
*Color.*—Near RHS Yellow-Green 144A.
*Strength.*—Moderate, highly flexible.
*Internode length.*—Approximately 1.5 cm.

FOLIAGE

Leaf:
*Arrangement.*—Simple, opposite. Sessile.
*Average length.*—Approximately 3.7 cm.
*Average width.*—Approximately 0.6 cm.
*Shape of blade.*—Elliptic.
*Apex.*—Acute.
*Base.*—Symmetrical cuneate.
*Margin.*—Entire.
*Texture of top surface.*—Glabrous, matte.
*Texture of bottom surface.*—Glabrous, matte.
*Quantity of leaves per lateral branch.*—Approximately 18.
*Color.*—Young foliage upper side: Near RHS Green 137B. Young foliage under side: Near RHS Green 138B. Mature foliage upper side: Near RHS Green 139A. Mature foliage under side: Near RHS Green 138B. Venation: Type: Pinnate, reticulate. Venation color upper side: Near RHS Yellow-Green 144B. Venation color under side: Near RHS Green 138B.

FLOWER

Natural flowering season: Spring.
Inflorescence description: Single bi-labiate flowers arranged on terminal racemes; flowers facing outward.
Flower longevity on plant: Individual flowers last approximately 1 week.
Quantity of flowers: 3 or 5 per raceme. Approximately 60 open inflorescences per plant.
Inflorescence size:
*Height.*—Approximately 6 cm.
*Diameter.*—Approximately 5 cm.
Pedicel:
*Length.*—Approximately 0.3 cm.
*Width.*—Approximately 0.1 cm.
*Color.*—Near RHS Yellow-Green 144A with flushing near Red-Purple 59A.
*Texture.*—Very lightly pubescent.
*Strength.*—Strong.
Flower bud: (just before opening)
*Length.*—Approximately 0.8 cm.
*Diameter.*—Approximately 0.5 cm.
*Shape.*—Ovoid.
*Color.*—Near RHS Red-Purple 59B.
*Texture.*—Pubescent.
Flowers:
*Flower form.*—Single bi-labiate.
*Flower diameter.*—Approximately 3.8 cm.
*Flower length.*—Approximately 3.2 cm.
*Flower throat diameter.*—Approximately 1.8 cm.
*Flower tube length.*—Approximately 1.6 cm.
*Quantity.*—1 upper lip, 2 lobed, 1 lower lip, 3 lobed, with palate.
*Arrangement.*—Lips fused at approximately 50% of length of flower.
*Upper lip, unfused portion.*—Length: Approximately 1.8 cm. Width: Approximately 1.6 cm. Apex: Obtuse. Margin: Entire. Texture: Inner side: Glabrous. Outer side: Pubescent. Appearance: Velvety. Color flower tube: At opening: Inner Surface: Near RHS Red-Purple 71A. Outer surface: Near RHS Red-Purple 72B. Mature: Inner Surface: Near RHS Red-Purple 71A. Outer surface: Near RHS Red-Purple 72C. Fading: Inner Surface: Near Purple N79D. Outer surface: Near Purple-Violet N80D with streaks near Purple N79D.
*Lower lip, unfused portion.*—Length: Approximately 1.0 cm. Width: Approximately 2.2 cm. Apex: Obtuse. Margin: Entire. Texture: Inner side: Glabrous. Outer side: Pubescent. Appearance: Velvety. At opening: Inner Surface: Near RHS Red-Purple 71A. Outer surface: Near RHS Red-Purple 72B. Mature: Inner Surface: Near RHS Red-Purple 71A. Outer surface: Near RHS Red-Purple 72C. Fading: Inner Surface: Near Purple N79D. Outer surface: Near Purple-Violet N80D with streaks near Purple N79D.
*Palate.*—Length: Approximately 1.3 cm. Width: Approximately 1.3 cm. Apex: Obtuse. Margin: Entire. Texture: Glabrous out edge with villous interior. Appearance: Velvety. Color: At opening: Near RHS Red-Purple 61A. Mature: Near RHS Red-Purple 59B, center stripe White N155B. Fading: Near RHS Red-Purple 72B.
Sepals:
*Quantity.*—Average 5.
*Appearance.*—Matte.
*Length.*—Approximately 0.7 cm.
*Width.*—Approximately 0.4 cm.
*Shape.*—Ovate.
*Apex.*—Acute.
*Base.*—Obtuse.
*Margin.*—Entire.
*Texture.*—Pubescent.
*Color.*—Inner Surface: Near RHS Green 137C. Outer Surface: Near RHS Green 137C.
Fragrance: Very faint.

REPRODUCTIVE ORGANS

Stamens:
*Number.*—4.
*Filament length.*—Approximately 1.3 cm.

*Filament color.*—Near RHS White N155B.

*Anther length.*—Approximately 1.3 cm.

*Anther color.*—Near RHS Yellow 9A.

*Anther shape.*—2 lobed ellipse.

*Pollen.*—Moderate.

*Pollen color.*—Near RHS Yellow 12A.

Gynoecium:

*Pistil.*—Number: 1. Length: Approximately 4.4 cm, non-fused, protrudes beyond petals. Style: Length: Approximately 1.3 cm. Color: Near RHS Red-Purple 70B.

*Stigma.*—Shape: Globular. Color: Near RHS Yellow 1A. Ovary color: Near RHS Yellow-Green 145C.

OTHER CHARACTERISTICS

Seeds and fruits: Not observed to date.

Disease/pest resistance: Neither resistance nor susceptibility to normal diseases and pests of *Antirrhinum* has been observed.

Temperature tolerance: Tolerates temperatures from approximately −1° C. to 32° C.

Drought tolerance: No tolerance for drought.

What is claimed is:

1. A new and distinct cultivar of *Antirrhinum* plant named 'AACOR01' as herein illustrated and described.

* * * * *